US008642320B2

(12) United States Patent
Lawrence et al.

(10) Patent No.: US 8,642,320 B2
(45) Date of Patent: *Feb. 4, 2014

(54) NON-PRECIPITATING BODILY FLUID ANALYSIS SYSTEM

(75) Inventors: Gregory M. Lawrence, Indianapolis, IN (US); Meredith Knight, Indianapolis, IN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 332 days.

This patent is subject to a terminal disclaimer.

(21) Appl. No.: 12/580,866

(22) Filed: Oct. 16, 2009

(65) Prior Publication Data

US 2010/0041066 A1 Feb. 18, 2010

Related U.S. Application Data

(60) Division of application No. 11/206,893, filed on Aug. 17, 2005, now Pat. No. 7,625,721, and a continuation-in-part of application No. 10/962,272, filed on Oct. 11, 2004, now Pat. No. 7,435,577.

(60) Provisional application No. 60/602,210, filed on Aug. 17, 2004, provisional application No. 60/541,681, filed on Feb. 3, 2004.

(51) Int. Cl.
*C12M 1/36* (2006.01)

(52) U.S. Cl.
USPC .................................... 435/287.7; 435/287.8

(58) Field of Classification Search
USPC ........................................................ 435/287.7
See application file for complete search history.

(56) References Cited

U.S. PATENT DOCUMENTS

| | | |
|---|---|---|
| 3,809,617 A | 5/1974 | Schmitt |
| 4,178,153 A | 12/1979 | Sodickson |
| 4,319,008 A | 3/1982 | Marze et al. |
| 4,362,078 A | 12/1982 | Ohnishi et al. |
| 4,477,575 A | 10/1984 | Vogel et al. |
| 4,549,655 A | 10/1985 | Forsythe, Jr. et al. |
| 4,738,823 A | 4/1988 | Engelmann |
| 4,774,192 A | 9/1988 | Terminiello et al. |
| 4,780,411 A | 10/1988 | Piejko et al. |
| 4,916,056 A | 4/1990 | Brown, III et al. |
| 4,943,522 A | 7/1990 | Eisinger et al. |
| 4,987,085 A | 1/1991 | Allen et al. |
| 5,013,339 A | 5/1991 | Mahoney et al. |
| 5,104,619 A | 4/1992 | de Castro et al. |
| 5,135,716 A | 8/1992 | Thakore |
| 5,145,583 A | 9/1992 | Angleraud et al. |
| 5,166,051 A | 11/1992 | Killeen et al. |
| 5,212,060 A | 5/1993 | Maddox |
| 5,240,862 A | 8/1993 | Koenhen et al. |
| 5,389,338 A | 2/1995 | Fish |
| 5,580,744 A | 12/1996 | Zweig |
| 5,597,532 A | 1/1997 | Connolly |
| 5,676,032 A | 10/1997 | Johnson |
| 5,695,947 A | 12/1997 | Guo et al. |
| 5,753,497 A | 5/1998 | Bernstein et al. |
| 5,888,827 A | 3/1999 | Kayahara et al. |
| 6,008,059 A | 12/1999 | Schrier et al. |
| 6,040,195 A | 3/2000 | Carroll et al. |
| 6,063,337 A | 5/2000 | Markart |
| 6,130,100 A | 10/2000 | Jobling et al. |
| 6,162,397 A | 12/2000 | Jurik et al. |
| 6,171,849 B1 | 1/2001 | Rittersdorf et al. |
| 6,194,164 B1 | 2/2001 | Matsui et al. |
| 6,287,867 B1 | 9/2001 | Harttig et al. |
| 6,340,589 B1 | 1/2002 | Turner et al. |
| 6,342,364 B1 | 1/2002 | Watanabe et al. |
| 6,440,306 B1 | 8/2002 | Ditter et al. |
| 6,488,828 B1 | 12/2002 | Bhullar et al. |
| 6,699,720 B1 | 3/2004 | Lee et al. |
| 6,759,190 B2 | 7/2004 | Lin et al. |
| 6,939,468 B2 | 9/2005 | Wang et al. |
| 7,135,150 B2 | 11/2006 | Noda |
| 2001/0005488 A1 | 6/2001 | Hirao et al. |
| 2002/0043095 A1 | 4/2002 | Mason et al. |
| 2003/0003522 A1 | 1/2003 | Goldman |
| 2003/0092102 A1 | 5/2003 | Rosen et al. |
| 2003/0143523 A1 | 7/2003 | Kato et al. |
| 2003/0166291 A1 | 9/2003 | Jones et al. |

(Continued)

FOREIGN PATENT DOCUMENTS

| | | |
|---|---|---|
| DE | 3217925 A1 | 11/1983 |
| DE | 3401932 A1 | 8/1985 |

(Continued)

OTHER PUBLICATIONS

Sugiuchi et al. "Homogeneous assay for measuring low-density lipoprotein cholesterol in serum with triblock copolymer and alpha-cyclodextrin sulfate", Clinical Chemistry, 1998, 44(3):522-531.*
Arfors et al. "Pharmacological characteristics of artificial colloids", Bailliere's Clinical Anaesthesiology, 1997, 11(1):15-47.*
In the US Patent and Trademark Office U.S. Appl. No. 10/962,272, Non-Final Office Action dated Mar. 5, 2007, 8 pages; response dated Jun. 5, 2007, 35 pages, and additional response dated Jun. 5, 2007, 10 pages.
In the US Patent and Trademark Office U.S. Appl. No. 10/962,272, Final Office Action dated Aug. 17, 2007, 8 pages; and response dated Nov. 16, 2007, 5 pages, including Request for Continued Examination.
In the US Patent and Trademark Office U.S. Appl. No. 10/962,272, Non-Final Office Action dated Feb. 25, 2008, 6 pages; and response dated Mar. 18, 2008, 8 pages.
In the US Patent and Trademark Office U.S. Appl. No. 11/206,590, Non-Final Office Action dated Aug. 29, 2008, 5 pages; and response dated Dec. 29, 2008, 7 pages.

(Continued)

Primary Examiner — Bin Shen
(74) Attorney, Agent, or Firm — Patton Boggs LLP (57) ABSTRACT

A bodily fluid analyzer including a dry test strip impregnated with a reagent providing a non-precipitating reaction to exclude non-desired analytes. The reagent complexes the non-desired analytes so they remain in solution but cannot participate in the test reaction. Red blood cells are removed from the detection area by slowing their vertical movement and stopping flow when the detection membrane is saturated.

11 Claims, 5 Drawing Sheets

(56) References Cited

U.S. PATENT DOCUMENTS

| | | |
|---|---|---|
| 2003/0175153 A1 | 9/2003 | Anaokar et al. |
| 2004/0126830 A1 | 7/2004 | Shull et al. |
| 2004/0167237 A1 | 8/2004 | Kim et al. |
| 2005/0003523 A1 | 1/2005 | Anaokar et al. |
| 2005/0170447 A1 | 8/2005 | Lawrence et al. |
| 2006/0062688 A1 | 3/2006 | Lawrence |
| 2006/0188392 A1 | 8/2006 | Tanaka et al. |

FOREIGN PATENT DOCUMENTS

| | | |
|---|---|---|
| DE | 19942928 A1 | 4/2001 |
| EP | 0260965 A | 3/1988 |
| EP | 0269876 A | 6/1988 |
| EP | 0389003 A | 9/1990 |
| EP | 0418169 A | 3/1991 |
| EP | 0511120 A | 10/1992 |
| EP | 0597268 A | 5/1994 |
| EP | 0753583 A | 1/1997 |
| JP | 02064455 | 3/1990 |
| WO | WO-00/73797 A | 12/2000 |
| WO | WO-03/025574 A | 3/2003 |
| WO | WO-03/058252 A2 | 7/2003 |

OTHER PUBLICATIONS

In the US Patent and Trademark Office U.S. Appl. No. 11/206,590, Final Office Action dated Apr. 15, 2009, 6 pages; and response dated Jun. 15, 2009, 9 pages.
In the US Patent and Trademark Office U.S. Appl. No. 11/206,590, Advisory Action dated Jul. 13, 2009, 3 pages; and response dated Sep. 14, 2009, including Request for Continued Examination.
In the US Patent and Trademark Office U.S. Appl. No. 11/206,590, Non-Final Office Action dated Sep. 29, 2009, 7 pages; and response dated Nov. 11, 2009, 8 pages.
In the US Patent and Trademark Office U.S. Appl. No. 11/206,893, Non-Final Office Action dated Feb. 18, 2009, 7 pages; and response dated May 18, 2009, 7 pages.
In the US Patent and Trademark Office U.S. Appl. No. 11/207,121, Non-Final Office Action dated Feb. 13, 2008, 11 pages; and response dated Mar. 14, 2008, 12 pages.
In the US Patent and Trademark Office U.S. Appl. No. 11/207,121, Non-Final Office Action dated Jun. 20, 2008, 14 pages; and response dated Sep. 22, 2008, 13 pages.
In the US Patent and Trademark Office U.S. Appl. No. 11/207,121, Final Office Action dated Dec. 24, 2008, 16 pages; and response dated Mar. 20, 2009, 12 pages, including Request for Continued Examination.
In the US Patent and Trademark Office U.S. Appl. No. 11/207,121, Non-Final Office Action dated Apr. 27, 2009, 17 pages; and response dated Jul. 27, 2009, 11 pages.
In the US Patent and Trademark Office U.S. Appl. No. 11/207,121, Final Office Action dated Nov. 27, 2009, 16 pages.
Feng et al.; "Adsorption of high density lipoproteins (HDL) on solid surfaces"; J of colloid and interface science; 1996; 177:364-371.
Nauck et al., "Methods of measurement of LDL-cholesterol: a critical assessment of direct measurement by homogeneous assays versus calculation", Clinical Chemistry, vol. 48, No. 2, 2002, pp. 236-254.
Santee; Am J Health-Syst Pharm 2002; 59; 1774-1779.
Sigiuchi et al.; "Direct measurement of high-density lipoprotein cholesterol in serum with polyethylene glycol-modified enzymes and sulfated alpha-cyclodextrin"; Clin. Chem.; 1995; 41(5):717-723.
Warnick et al., "Evolution methods for measurement of HDL-cholesterol: from ultracentrifugation to homogeneous assays", Clinical Chemistry, vol. 47, No. 9, 2001, pp. 1579-1596.
In the US Patent and Trademark Office U.S. Appl. No. 11/206,590, Final Office Action dated Feb. 3, 2010, 7 pages.
In the US Patent and Trademark Office U.S. Appl. No. 11/207,121, Final Office Action dated Mar. 9, 2011, 12 pages.
In the US Patent and Trademark Office U.S. Appl. No. 11/207,121, Non-Final Office Action dated Jul. 27, 2012, 15 pages.
In the US Patent and Trademark Office U.S. Appl. No. 11/933,292, Non-Final Office Action dated Nov. 10, 2010, 14 pages.
In the US Patent and Trademark Office U.S. Appl. No. 11/933,292, Non-Final Office Action dated Oct. 3, 2012, 12 pages.
In the US Patent and Trademark Office U.S. Appl. No. 12/772,707, Non-Final Office Action dated May 29, 2010, 8 pages.

\* cited by examiner

NON-PRECIPITATING BODILY FLUID ANALYSIS SYSTEM

CROSS-REFERENCE TO RELATED APPLICATIONS

This application is a divisional of U.S. patent application Ser. No. 11/206,893 filed Aug. 17, 2005, now U.S. Pat. No. 7,625,721 issued Dec. 1, 2009, which claims the benefit of U.S. Provisional Application No. 60/602,210 filed Aug. 17, 2004, and which is a continuation-in-part of U.S. patent application Ser, No. 10/962,272 filed Oct. 11, 2004, now U.S. Pat. No. 7,435,577 issued Oct. 14, 2008, which claims the benefit of U.S. Provisional Application No. 60/541,681 filed Feb. 3, 2004. All of the above patent applications, both provisional and non-provisional, are hereby incorporated by reference to the same extent as though fully contained herein.

BACKGROUND OF THE INVENTION

The invention in general relates to bodily fluid analysis systems including a disposable test strip and a spectrophotometric sensing device, with particular application to on-site testing of particular analytes in blood.

The level of certain analytes in blood and other body fluids is often used to diagnose disease, determine disease risk factors, monitor the course of a therapy, or determine the presence of illicit drugs. For example, analytes carried in blood have been evaluated to determine various cholesterol and triglyceride levels as a significant indicator of risk of coronary heart disease.

The blood analysis necessary to determine bodily fluid analytes, such as total cholesterol, high density lipoprotein cholesterol (HDL), low density lipoprotein cholesterol (LDL), and triglycerides, may be performed in clinical setting in a laboratory or on site using dry test strips. In the laboratory, the blood is centrifuged to separate the red blood cells from the plasma, and carefully controlled chemical tests in test tubes are performed to determine the concentration of analytes. Dry test strips utilize several membrane layers to separate red blood cells from blood plasma, react the plasma with a particular reagent or reagents, and obtain a signal indicative of the concentration of a particular analyte, which is usually a spectrophotometric signal. See, for example, U.S. Pat. No. 4,774,192 issued Sep. 27, 1988 to Terminiello et al.; U.S. Pat. No. 4,477,575 issued Oct. 16, 1984 to Peter Vogel et al.; U.S. Pat. No. 5,104,619 entitled "Disposable Diagnostic System"; U.S. Pat. No. 5,135,716 issued Aug. 4, 1992 to Tatin B. Thakore; U.S. Pat. No. 5,166,051 entitled "Membranes, Membrane Overlays, For Exclusion of Erythrocytes, And Method Of Immunoassay of Whole Blood Analytes"; U.S. Pat. No. 5,597,532 issued Jan. 28, 1997 to James Connolly; U.S. Pat. No. 6,171,849 issued Jan. 9, 2001 to Walter Rittersdorf et al.; U.S. Pat. No. 6,759,190 issued Jul. 6, 2004 to Jinn-Nan Lin et al., United States Patent Application Publication No. US2004/0126830 published Jul. 1, 2004 on an invention of Bruce Shull et al.; and United States Patent Application Publication No. US2005/0003523 published Jan. 6, 2005 on an invention of Sunil Anaokar et al.

All of the above systems depend on precipitation and/or filtration to separate the unwanted components from the analytes to be tested. For example, if HDL is the desired analyte, the other lipoproteins are reacted to for a precipitate and are filtered from the plasma using filter membranes. However, the precipitates tend to block the pores in the system and impede the flow the desired analytes also, which reduces the amount of the desired analytes that reach the reaction area, and thus reduces the accuracy of the test. The conflict between the need for good separation of unwanted components from the analytes and the accuracy problems associated with such separation has caused the accuracy of the test strip/spectrophotometric systems to plateau, and has limited the usefulness of this art. Thus, there is a need for a test strip/spectrophotometer architecture that can improve the capabilities of the dry strip technology system and that yield more accurate readings.

BRIEF SUMMARY OF THE INVENTION

The present invention solves the above problem by providing a dry test strip chemistry that reacts the unwanted components of the bodily fluid into complexes that do not participate in the test reaction. The complexes remain free to flow, and thus do not clog membranes or filters.

The invention further comprises a method of determining a characteristic of a selected one of a plurality of analytes in a bodily fluid, the method comprising: providing the bodily fluid containing the selected analyte and one or more non-selected analytes; reacting the selected one of the analytes with a reactant to provide a calorimetric indication of the characteristic; and prior to the reacting, preventing the non-selected analytes from participating in the reaction, without precipitating the non-selected analytes.

These and other objects and benefits of the invention will become apparent from the following written description and accompanying figures.

DETAILED DESCRIPTION OF THE INVENTION

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains. It should also be understood that, in accordance with the patent law, the drawings are not intended to be precise engineering drawing of the invention, but rather are only intended to illustrate the invention. For example, the scale of the drawings and relative size of the various parts are generally altered so as to better illustrate the invention within the constraints of a written document such as this.

Figure 3:
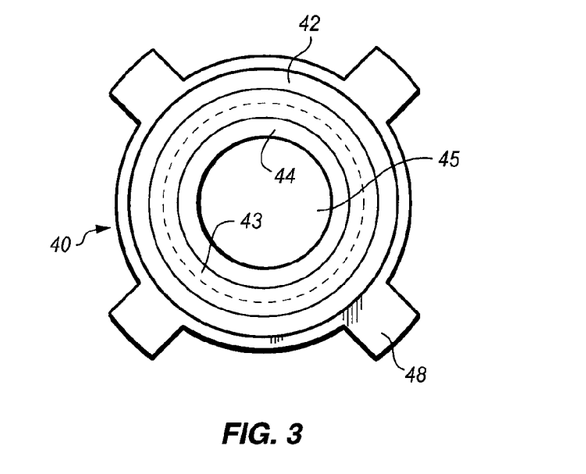
FIG. 3 is a bottom plan view of the cap portion of the test strip assembly of FIG. 1.

An exploded perspective view of an exemplary test assembly 20 according to the invention is shown in FIG. 3. Test assembly 20 includes a preferably elongated test strip carrier body 30, a test strip 50, and a test strip holder 24. Test strip holder 24 includes a holder base portion 60 and a holder cap 40. Carrier body 30 includes a grip portion 26, openings 32 and 34, sensor port or test opening 36, and holder base 60. Grip portion 26 includes raised ribs 28 which permit the fingers to easily grip the carrier body 30.

Figure 1:
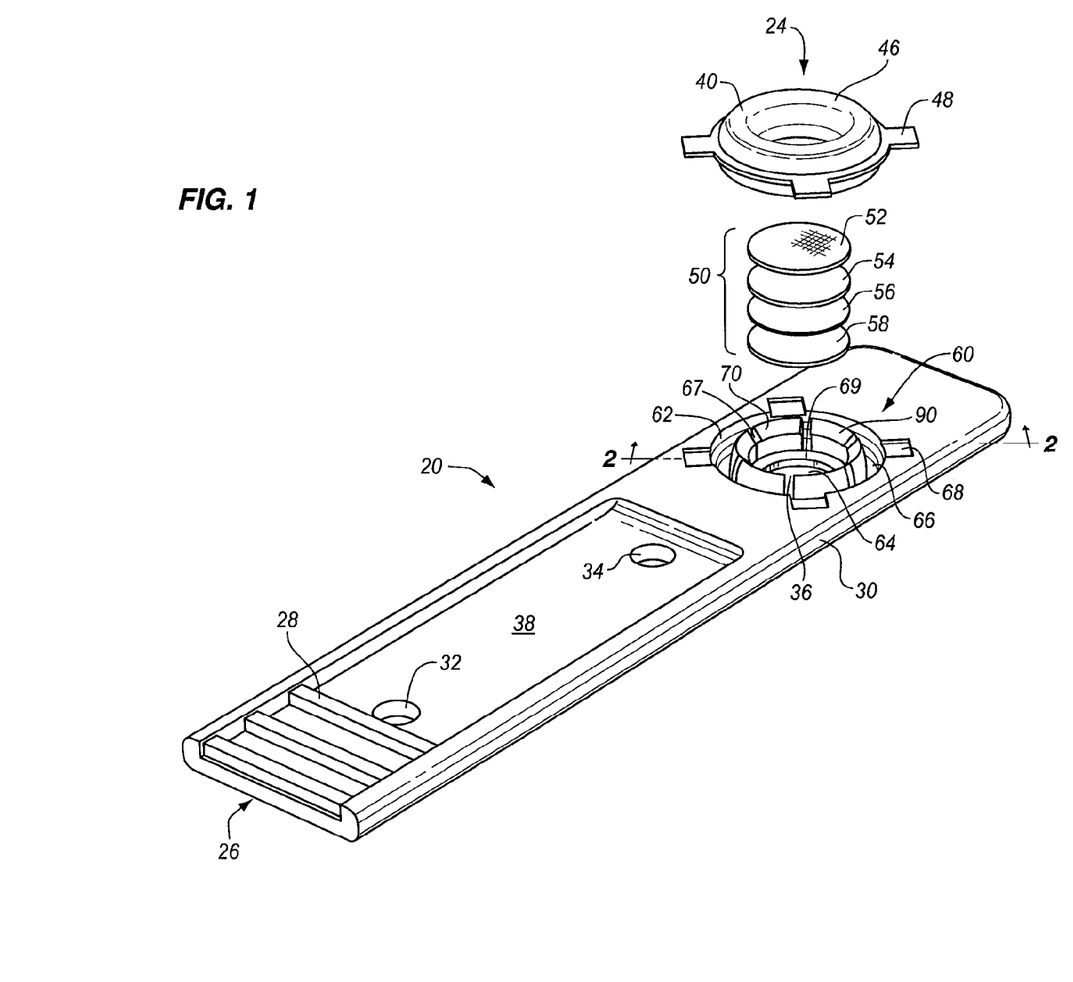
FIG. 1 is an exploded perspective view of the preferred embodiment of a test strip assembly according to the invention.
Figure 2:
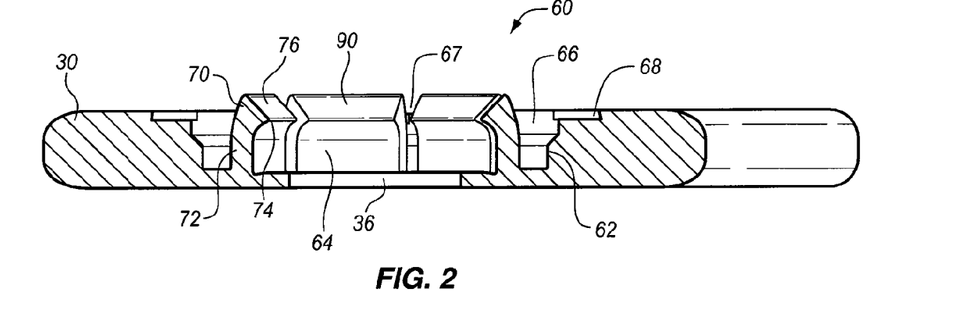
FIG. 2 is a cross-sectional plan view of test strip of FIG. 2 taken through the line 2-2 of FIG. 1.
Figure 4:
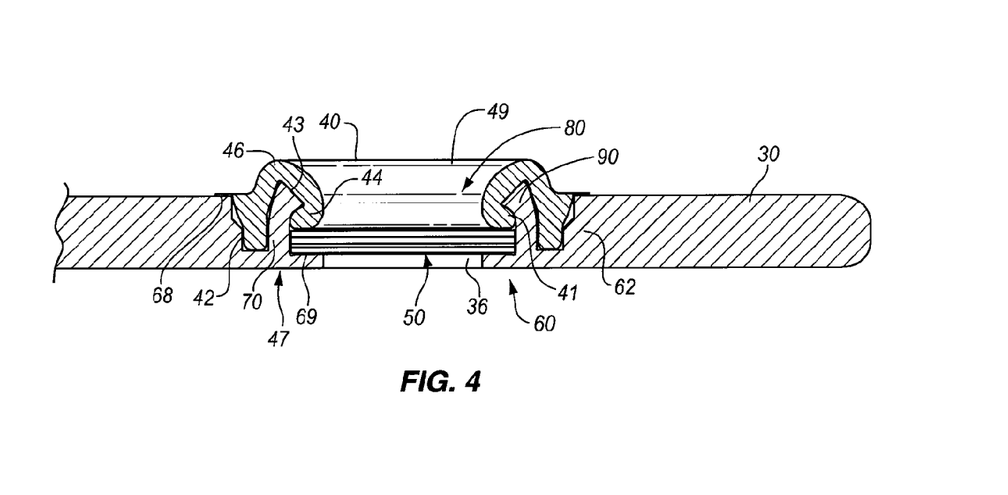
FIG. 4 is cross-sectional view of the test strip holder of FIG. 1.

The holder base 60 is shown in FIGS. 1, 2, and 4. FIG. 1 shows a perspective view, FIG. 2 shows a partially cross-sectioned side view, and FIG. 4 shows a cross-sectional view with the cap 40 in place over holder base 60. Preferably, holder base 60 includes a well 62 formed in body 30, alignment recesses 68, and retainer 90, which is preferably flexible. Well 62 has an upward sloping well wall 83 completely encircling the test opening (sensor port) 36. Retainer 90 preferably comprises fingers 70 and separates well 62 into an inner portion 64 which forms a test strip well 64 and an outer portion 66, which is preferably relatively small in volume, being just big enough to allow fingers 70 to flex. In this disclosure, the term "encircle" does not necessarily mean the encircling structure forms a circle, but rather it has the broader common meaning of "to pass completely around". In the preferred embodiment, however, the well 62 and fingers 70 do form a circle. In the preferred embodiment, there are four alignment recesses 68 and six fingers 70, though the invention contemplates that any number suitable to perform the functions described below may be used. Each finger 70 includes a stem portion 72, a hook portion 74, and a ramp portion 76 that is preferably formed at an acute angle to a vertical line perpendicular to the plan of body 30. Fingers 70 are separated by channels 67. The bottom of well 62 forms a test strip support 69 around port 36 on which, as will be seen below, the test strip 50 rests, as best shown in FIG. 9.

Cap 40 is shown in FIGS. 1, 3, and 4. FIG. 1 shows a perspective view, FIG. 3 shows a bottom plan view, and FIG. 9 shows a cross-sectional view of the cap 40 in place over the holder base 60. Cap 40 includes an outer foot 42, an inner flange 44, and a connecting portion 46, which, as will be seen below, forms the brim 49 of a bodily fluid container 80. The outer foot 42 and inner flange 44 have different lengths, with the inner flange being shorter. The difference in lengths is less than the thickness of test strip assembly 50, so that the inner flange 44 and test strip support 69 engage strip 50 sufficiently to secure it in place. Preferably, the difference is sufficient so that flange 44 and test strip support 69 compress strip 50 between them. The bottom 43 of connecting portion 46 is shaped to form a groove 47 into which fingers 70 fit snuggly. A lip 41 is formed on flange 44 (FIGS. 8 and 9) which engages hook 72 to latch cap 40 on holder base 60. The distal end 84 of flange 44 is smooth and rounded so as not to damage test strip 50.

Test strip 50 is shown in FIGS. 1 and 4, and is preferably formed of a plurality of layers. Each layer performs a specific function as required by each specific test. Generally, there is a "spreading" layer 52 to ensure even distribution of the whole blood sample; a "separation" layer 56 to obtain a clarified plasma/serum sample; a layer or layers 54 to hold specific test reagents in sequence as needed by each specific assay; and a final "color" or "test reaction" layer 59 to provide a matrix on which a specific color or test reaction will develop for each specific test. The order of the layers can vary. For example, the separation layer may come before or after the reagent layer(s). The details of the test strip layers is described below.

The test strip assembly 20 is assembled as shown in FIGS. 1 and 4. A cone-shaped inserter (not shown) presses down on the ramps 76 of the fingers 70 and spreads them sufficiently to drop the assembled test strip 50 onto test strip support 69. Cap 40 is then pressed home on retainer 90, with fingers 70 forced into groove 47, compressing test strip 50 sufficiently to hold it in place.

The carrier body 30, holder base 60, and cap or cover 40 are preferably made of plastic or other suitable material. The preferred plastics are polypropylene or nylon, though other plastics may be used. Preferably, the plastic parts are injection molded, and cap 40 is sonic welded to holder base 60 at locator tabs 68. Thus, the placement tabs enable the cap to be welded without contact with the main body of cap 60. Preferably, the plastic parts, particularly the cap 40, are color-coded to correspond to the particular test, such as HDL, LDL, total cholesterol, etc., for which the test strip assembly, such as 50, is designed.

Preferably, for the exemplary HDL test, there are four layers 52, 54, 56, and 58, best shown in FIG. 3. Top layer 52 is preferably a spreading layer designed to disperse the bodily fluid rapidly in all horizontal directions so that it is distributed evenly across the test strip 50. Another function of layer 52 is to distribute the pressure exerted by the cap or cover 40, 170, 240, 340 as evenly as possible across the entire area of the lower layers, such as 54, 56, and 58. Thus, it should be fairly stiff. Preferably, it should be sufficiently stiff to provide a flat surface; that is, a surface with a bulge in the middle of less than 0.002 inches when the cap is in place, but sufficiently flexible to allow the cover to seal the edge of the membranes. Preferably, layer 52 is made of a mesh with either an open or closed weave. Some suitable woven mesh materials are SEFAR™ type 76 SK 022, which is an open mesh with a close weave, or a Tetko™ mesh, which is a closed mesh, though other suitable and equivalent materials may also be used. An open mesh works by letting the sample through, while a closed mesh works by adhesion of the sample to the mesh threads, i.e., by wicking. Thus, different parameters are required for the different meshes. If an open mesh is used, preferably more than 40% of the total area should be open, and more preferably 50%. If the mesh is a closed mesh, the open area should be 15% or less and more preferably 10% or less.

The next layer 54 contains the reagents that interact with the non-desired analytes that would compromise the calorimetric test to be performed in layer 58 so that these analytes do not participate in the calorimetric reaction. For example, if the calorimetric test in layer 58 is to be a test for HDL, analytes, such as LDL (low density lipoproteins), VLDL (very low density lipoproteins), ILDL (intermediate density lipoproteins), and chylomicrons (big, triglyceride-rich lipoproteins) that may make the test less accurate or reliable are interacted with in some way that prevents them form participating in the calorimetric reaction in layer 58. Preferably, the reaction is one in which these analytes are bound in clusters within a compound that prevents them from reacting. An example of the specific reagents are given in Example 1, below.

Layer 54 is also preferably a depth filter, which functions to reconstitute the reagent; that is, get the dried reagent into solution. A key feature of this layer 54 is that it includes many small fibers, and thus it has a large surface area. Preferably, the fibers are random, that is, they are not organized as in a weave. This type of filter is often referred to as a conjugate relief pad, wicking pad, sample pad, or prefilter. The surface area is preferably such that the wicking rate is below 8 seconds per two centimeters. Preferably, the surface area should be such that after wetting with the reagent and drying, the layer holds a weight of dry reagent equal to the membrane weight itself. Preferably, the weight of the dry agent should not be lower than 75% of the weight of the membrane and not above 125% of the weight of the membrane. Since the reagent is on the surface of the fibers, the large surface area helps to reconstitute the reagent faster, since there is a larger area of reagent exposed to the solvent. Preferably, the average pore size of this layer is controlled to optimally control flow through the layer so that the bodily fluid remains long enough to reconstitute the reagent, but not so long as to delay or otherwise hinder the test in layer 58. The controlled pore size in combination with the large surface area helps to limit or retard the movement of the solute in the vertical direction, so that it remains in the material longer, and thus has more time to dissolve the reagent. Preferably, layer 54 is made of a non-woven, fibrous material such as a hydroxylated polyester, preferably a polyhydroxylated polyester. Suitable such materials are membranes made by Pall Life Sciences, such as Accuwick Ultra™. Preferably, the membrane is inserted with the bumps side down.

The purpose of the next layer 56 is preferably to remove red blood cells from the analyte liquid and to further add to the reagent/solvent contact time to continue the process of getting the reagent into solution. It is preferably made of an asymmetrically porous material; that is, the pore size varies through the material. Preferably, the side with the large pores is up. In the preferred embodiment, it has a pore size of between 250 microns and 350 microns, and more preferably 300 microns on the sample-receiving side, and a pore size of between 0.5 microns and 10 microns, and preferably 3 microns, on the detection side. The preferred material is an asymmetric polysulfone such as is BTS-SP-300 or BTS-SP-200 available from Pall Life Sciences, or other suitable materials may be used. Other suitable materials are lechtin-coated graphite fibers, ruthenium oxide fiber, and other materials known in the art. The asymmetric nature of the layer 56 is effective in removing red blood cells while continuing the movement of the solvent and reactant downwards. In the preferred embodiment, it removes the red blood cells by slowing them as they percolate through the tortuous path of the pores. As the pores get smaller, the red blood cells may also become entangled in the fibers, but this happens gradually and relatively randomly throughout the layer, rather than collecting all at one level within the test strip, as they would in a conventional filter with a single pore size; such collecting all at one level tends to block fluid flow. The relatively random entrapment of the red blood cells leaves open capillary paths through the material. Such capillaries assist in drawing the fluid downward through the test strip 50, particularly since the capillaries become smaller in that direction. As will be seen more clearly below, however, it is only necessary to slow the red blood cells to separate them. That is, because the bottom of container 80 is essentially closed, flow stops when the layer 58 becomes saturated. If flow stops and the red blood cells are still in the upper layers, they will remain there.

Bottom layer 58 is the detection layer and contains the detection reagent. It is preferably made of a hydrophobic material which has sufficient surface tension with the analyte bodily fluid so that the fluid will not flow past it. In the preferred embodiment, the test strip assembly layers 52-58 are circular and are all of the same diameter, though other shapes and sizes may be used. The preferred detection layer 58 is the Biodyne™ A membrane available from Pall Corporation with the total cholesterol formulation described in United States Patent Application Publication US 2004/0126830 on application Ser. No. 10/663,555 filed Sep. 16, 2003, which is hereby incorporated by reference to the same extent as though fully disclosed herein. This membrane is a nylon membrane in which the net charge can be controlled by changing the pH. As disclosed in the foregoing reference, the reagents are Trinder reagents which include enzymes, such as cholesterol oxidase, perosidase, and cholesterol esterase, that react with cholesterol to effect a color change which can be detected optically.

Figure 5:
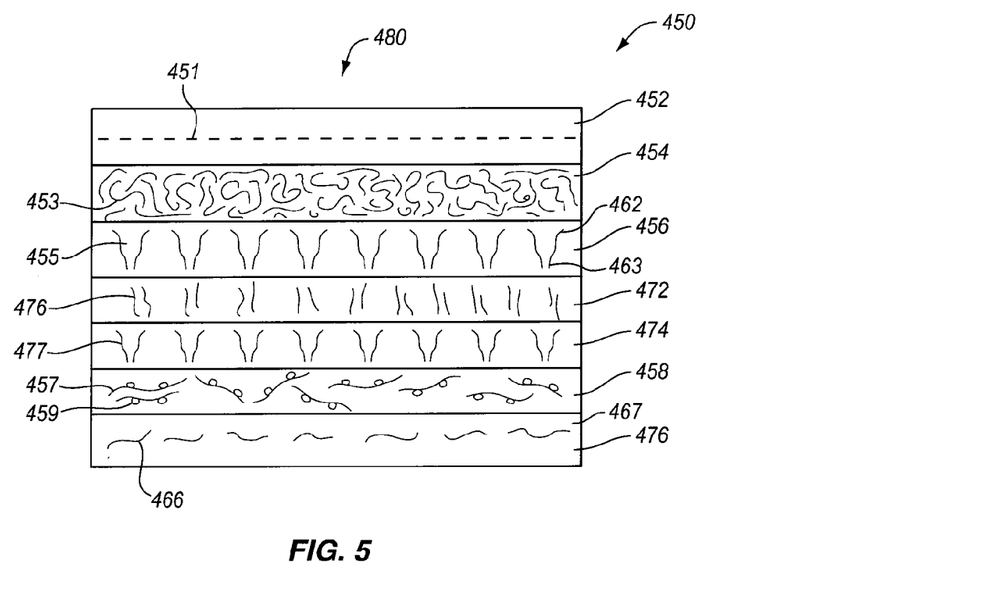
FIG. 5 is a cross-sectional view of a test strip element according to the invention illustrating some of the features of the invention.

FIG. 14 is a cross-sectional view of an alternative test strip assembly 450 according to the invention illustrating some of the features of the invention. Test strip assembly 450 includes layers 452, 454, 456, 472, 474, 458, and 470. Layer 452 comprises a woven mesh 451. Weaves tend to cause fluid to flow more easily along the weave rather than through it, and thus, if the weave 451 is horizontal, layer 454 will tend to distribute the bodily fluid across the layer. Layer 454 can either be a material that traps and holds red blood cells, such as Tuffglass™, or it can be a material such as Accuwick Ultra™, that merely slows the red blood cells. Preferably, it includes fibers 453 that are relatively randomly distributed. That is, the fibers 453 are not organized as in a weave. Preferably, the fibers are also very thin, and thus the layer 454 has a large surface area. This type of material holds a relatively large amount of fluid, and the fluid is in contact with a lot of area. This material functions well to get reagents on the surface of the fibers into solution. Layer 456 is a membrane material. Membranes have pores that are relatively organized. The preferred material of layer 456 is an asymmetric membrane, which means that the pores vary in size. Preferably, in layer 456 the pores are larger at the upper end 462 of the material and smaller at the lower end of the material 463. Note that for illustration purposes the pores are shown in layer 456 as single channels with a varying diameter, but in fact the "channels" are preferably not well-defined and branch in all directions. The important characteristic is that the dimensions of the pores are larger at end 462 than at the other end 463. In the preferred embodiment, the membrane used is more like a depth filter at the top; that is, the material is fiber-like and amorphous. That is, the fibers are disorganized, i.e., essentially randomly distributed. At the bottom it is membranous, with a definite pore size. The layer can be engineered to be more or less depth filter-like at the top and more or less like and absolute membrane at the bottom. The more it is like a depth filter, the more capacity it has. The preferred material is a polysulfone.

Layers 472 and 474 are preferably optional layers used in controlling timing of the reconstitution of the reagent in layer 456. For example, membrane 472 may be a Supor™ 1200 untreated membrane. This example has relatively large 1200 micron pores. It is used to slow down the percolation of the analyte liquid through the assembly to give the reagent introduced in layer 456 more time to dissolve. The smaller the pores in layer 472, the more it slows down the analyte. Layer 474 is an optional layer, preferably having asymmetrical pores 477, that may be identical to layer 456, and is included if it is desired to put more reagent in solution, or to put less reagent in layer 456 so that it dissolves more easily. Layer 458 is a reagent layer which is illustrated by showing a fiber 457 with a reagent 459 on its surface. This reagent is the calorimetric reagent that reacts with the analyte to produce the color, the reflectance of which provides the test result. Layer 476 is a layer in which the individual fibers 466 are preferably hydrophobic, which means they tend to repel water; that is, preferably, water has a high surface tension on the material. Water will tend not to penetrate this material. However gas, such as air, will pass easily through this material. Preferably, the material of layer 476 is an open pore material, and/or also holds a relatively large amount of fluid, as compared to membranes such as 456. However, it also may be an asymmetric membrane with the larger pores on the upper side 467. Such a material tends not to hold large amounts of fluid, but makes the fluid available to the reaction layer 458, as will be discussed in more detail below. Layer 476 is also preferably very thin and/or transparent, particularly when it is saturated with liquid, so that the color in layer 458 can be sensed through it. In the embodiments of FIGS. 2-13, the features of layers 458 and 460 were combined.

The test strip operates generally as follows. A drop of bodily fluid, such as blood, is placed within the sample application port 45 of cap 40. It is evenly dispersed across the opening by test strip layer 52 and percolates vertically downward. The pall membrane 54 separates the unwanted material, such as the red blood cells, from the rest of the fluid, such as the serum. The red blood cell filtration/reagent membrane 56 includes reagents that react with undesired analytes that would compromise the test in membrane 58. For example, if the test in membrane 58 is for HDL, the LDL, ILDL, VLDL, and chylomicron portions of the serum are complexed in membrane 56. The membrane tends to slow or retain the complexed lipoproteins, but allows the HDL to pass to reagent layer 58. The HDL reacts in reagent layer 58 to turn the layer a predetermined color, which is detected by spectrophotometer device 10. However, it is not necessary that membrane 56 retains or even slows the complexed undesired lipoproteins. The complexing itself prevents the undesired analytes from participating in the reaction in test membrane 58 and thus takes these analytes out of the reaction that determines the color. A more detailed description of the chemicals used in the test strip layers and the chemical reactions that take place in the test strip layers will be presented below.

The chemistry of the test strip element 50, 450 is selective of specific lipoproteins by being able to keep them from reacting in layer 58, 458 and/or enhancing their reaction in layer 58, 458 depending on differences between the size, mass density, and surface charge density of the HDL, LDL, ILDL, VLDL, and chylomicron lipoproteins. As known in the art, the HDL lipoproteins are the smallest, have the greatest mass density, and the highest surface charge density; the VLDL and chylomicrons are the largest, have the smallest mass density, and the lowest surface charge density; and the others are in between. It is sometimes helpful to think of HDL as a baseball, the LDL as a small beach ball, and the VLDL as a very large beach ball. The chemistry for an HDL test strip relies on a complex including a polyanion, a divalent metal, and the lipoproteins. Preferably, the polyanion is a negatively charged polymer. Preferably, the polymer is dextran sulphate. The divalent metal forms a salt bridge between the lipoprotein and creates a polymer complex that shields the cholesterol from surfactant emulsification required for it to participate in the Trinder enzymic reactions that create the color change in the layer 58, 458. For this complex to be selective between the various lipoproteins, the molecular weight, charge density, and branching of the anionc polymer must all be considered. To be selective without precipitation, the molecular weight should preferably be between 50,000 and 8,000; more preferably between 25,000 and 10,000; and most preferably between 18,000 and 12,000. The charge density should roughly match the lipoproteins you are trying to bind, with the proviso that the more branching there is, the less the charge that is required. With these parameters adjusted for LDL, ILDL, VLDL molecules, and chylomicrons, the complex does not form well with the HDL, because the polymer molecules are too large and possess too small a surface charge density to bind easily with the small, dense HDL molecule. However, the polymer molecules bind easily with the LDL, ILDL, VLDL molecules, and chylomicrons, complex them, and take them out of the reaction. Thus, the reaction occurs essentially only with the HDL molecules, and results in an effective HDL assay.

The chemistry for an LDL assay is similar, but somewhat more complicated due to the fact that the LDL is intermediate between the HDL and ILDL, VLDL molecules. This chemistry is disclosed in detail in copending and co-owned U.S. patent application Ser. No. 10/962,272 filed Oct. 11, 2004, now U.S. Pat. No. 7,435,577 issued Oct. 14, 2008, on an invention of Greg Lawrence and John Pasqua, which patent is hereby incorporated by reference to the same extent as though fully disclosed herein. In this chemistry, the anionic polymer is the same, but a surfactant is selected that is specific to the LDL. That is, a destabilizing agent specific to the LDL is added that enables the LDL to react more quickly with the Trinder enzymes. As disclosed in the above-referenced application, this destabilizing agent may be a glycol, such as polypropylene glycol or polyethylene glycol, and is preferably a polyoxyethylene-polyoxypropylene-polyoxyethylene hybrid, and more preferably such a hybrid having a molecular weight between 2,100 and 6,000, and most preferably with a preponderance of polyoxyethylene. Such destabilizers act by loosening the bonds just beneath the surface of the lipoprotein, penetrating the surface, and expanding it to permit the entry of surfactants which solubilize the cholesterol and make it available for the Trinder reactions. Because of the high density surface of the HDL, they do not penetrate it easily. In fact, the compounds tend to complex with the surface of the HDL molecule and isolate it from the Trinder reactants. The compounds are able to penetrate the ILDL, VLDL, and chylomicron molecules, but because these molecules are so large, the effect is diminished.

The choice of surfactant is based on a number of factors. As indicated, the properties of the surfactant are such that the complexes to be measured are selectively emulsified. Further, the destabilizing compounds, such as polypropylene glycol, are not very water soluble. Thus, to get them to act on the lipoproteins, they are preferably emulsified by a surfactant. If the surfactant is too strong in the LDL assay, non-LDL lipoprotein cholesterols are emulsified and subsequently react, and the process is non-selective. Thus, a gentler surfactant, such as CHAPS (3-{[3-Cholamidopropyl]dimethylammonio}3-propane-sulfonate) or other pluronic non-ionic surfactants should be used. A stronger surfactant, such as Triton X-100, can be used in the HDL assay because the ILDL, VLDL, and chylomicron molecules are not destabilized.

EXAMPLE I

TABLE A

| Accuwick Ultra Solution ID SolOct13-04 A4 | | | |
|---|---|---|---|
| Item Description | Lot Number/Batch | Total Mass g | % Used |
| Lab D.I Water | | 177.34 | 88.6688 |
| Dextralip 50 | Warnick & Co. 00501 Lot 99123 | 1.50 | 0.7500 |
| Mops Buffer | | 1.16 | .5813 |

TABLE A-continued

Accuwick Ultra
Solution ID SolOct13-04 A4

| Item Description | Lot Number/Batch | Total Mass g | % Used |
|---|---|---|---|
| Sorbitol | Sigma-Item S-7547 Lot 70K0936 | 20.00 | 9.9999 |
| Ph Adjustment | 5N NaOH/HCl | Adjust pH to target 7.20 | |
| Total | | 200.00 | |
| Cloud Point | 1% MOPS = 48 mM | Used 48 mM TRIS | |

TABLE B

Accuwick Ultra
Solution ID SolOct13-04 A4

| Item Description | Lot Number/Batch | Total Mass g | % Used |
|---|---|---|---|
| SolOct13-04 A1 (Table A) | | 29.54 | 98.4667 |
| MgC12*6H20 | Sigma: Item M-9272; Lot 70K09321 | 0.46 | 1.5333 |
| pH Adjustment | 5.0N NaOH/HCl | Adjust pH to target 7.20 | |
| Total | | 30.00 | |
| Cloud Point | 1% MOPS - 48 mM | Used 48 mM TRIS | |

TABLE C

BTS Formulation
Solution ID SolMar28-05 C

| Item Description | Lot Number/Batch | Total Mass g | % Used |
|---|---|---|---|
| Lab D.I Water | | 276.00 | 92.0000 |
| Mops Buffer | Signma M-1254 Lot 71K5450 | 3.00 | 1.0000 |
| Sorbitol | Sigma-Item S-7547 Lot 70K0936 | 9.00 | 3.0000 |
| Sucrose | Sigma-Item S-5016 | 9.00 | 3.0000 |
| MgC12*6H20 | Sigma: Item M-9272; Lot 70K09321 | 3.00 | 1.0000 |
| PVA 30-70K | | 8.00 | 2.6667 |
| pH Adjustment | 5N NaOH/HCl | Adjust pH to target 7.20 | |
| Total | | 300.00 | |
| Cloud Point | | | |

A sheet of material 54 was made in the following manner. A dextran sulphate sodium salt in the form of Dextralip™ 50, which has a molecular weight of about 40,000, MOPS buffer (3-morpholinopropanesulfonic acid) and sorbitol were added to deionized (DI) water in the amounts shown in Table A, mixed, and adjusted for pH as indicated in the table to make a stock solution. As known in the art, pH is adjusted as necessary to the alkaline side with NaOH, and to the acid side using HCL. Then to 29.54 grams of the stock solution, MgCl$_2$.6H$_2$O was added in the amount shown in Table B, and the pH was again adjusted. The Accuwick Ultra™ material was dipped into this solution and was hung vertically to allow the excess solution to drip off the material. The material was then dried horizontally in a drying tunnel at 85° F.-95° F. for 9 minutes to 18 minutes.

A sheet of material 56 was made in the following manner. Mops buffer, sorbitol, sucrose, MgCl$_2$.6H$_2$O, and polyvinyl alcohol 30-70K were added to DI water in the amounts shown in Table C. A sheet of BTS material was dipped into this solution and was hung vertically to allow the excess solution to drip off the material. The material was then dried horizontally in a drying tunnel at between 70° F.-90° F. and more preferably between 75° F.-85° F., for 9 minutes to 18 minutes.

A sheet of material 58 was made as follows. A stock solution of Cholesterol Foundation was made with 800 g DI water, 30 g sodium citrate (dihydrate), 60 g of polyvinyl propylene K-30, 2 g benzoic acid, 4 g BSA, and 1.47 g EDTA (disodium, dihydrate). The pH was adjusted to about 5.5, and then sufficient DI water was added to make 1000 ml of solution. Then a solution was made with 200 g DI water, 0.771 g Triton X-100, 532 g cholesterol foundation, 13.88 g BSA, 95.61 g 10% Gantrez AN-139 (w/v), 19.82 g CHAPS (3-{[3-Cholamidopropyl]dimethylammonio}3-propane-sulfonate), and 37.01 g sucrose, and the solution was adjusted to a pH of about 5. Then 0.116 g of potassium ferrocyanide, 0.37 g TOOS, 4.63 g MaOS, 148 KU cholesterol oxidase, 462.6 KU perosidase, 92.5 KU cholesterol esterase, and 4.163 g 4-Amino antipyrine, and the pH of the solution was adjusted to about 5.4. Enough DI water was added to make 1000 ml of solution. A sheet of Biodyne™ A material was dipped into this solution and was hung vertically to allow the excess solution to drip off the material. The material was then dried horizontally in a drying tunnel at between 90° F. and 100° F. for 9 minutes to 18 minutes.

Figure 6:
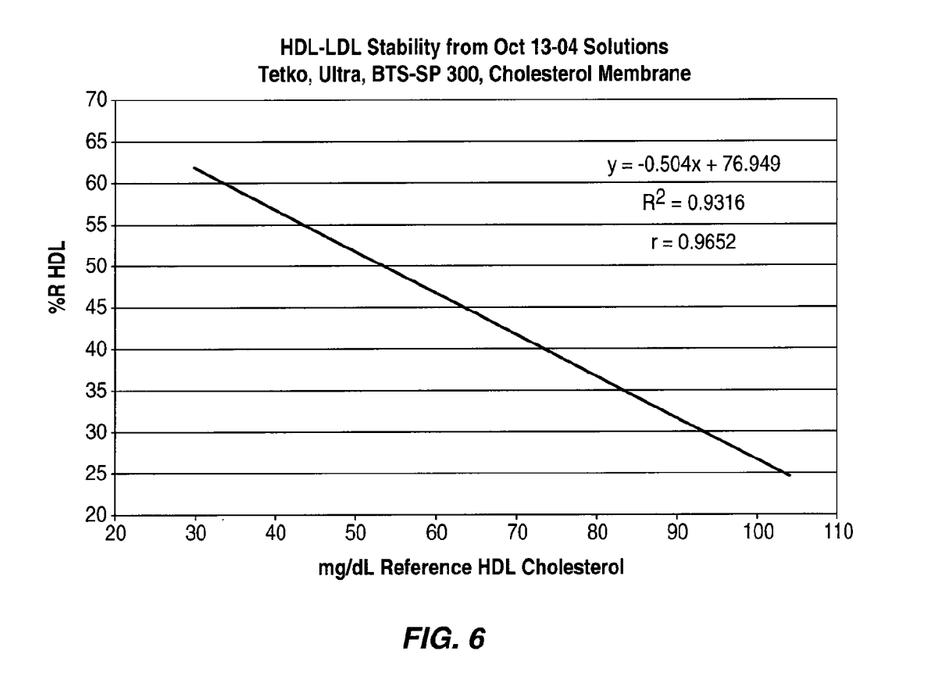
FIG. 6 is a graph showing the data-derived baseline reflectance versus mg/dl HDL curve from which a reflectance test according to the invention can be generated.

A test strip assembly 50 was made by assembling a sheet of SEFAR™ type 76 SK 022 and the above three sheets. Circular blanks were cut out and were inserted in a test assembly 20 as shown in FIGS. 3-9. In a manner known in the art, a curve as shown in FIG. 6 was then constructed using reflectance measurements from a standard laboratory test for HDL. As also known in the art, the curve of FIG. 6 was then used to program a Bioscanner 2000 reader available from Polymer Technology Systems, Inc., Indianapolis, Ind. The reader was then successfully used to directly read HDL concentrations in milligrams per deciliter (mg/dl) from a test assembly as described above.

EXAMPLE II

TABLE D

Accuwick Ultra or other Depth Filter Treatment
Solution Fractionation: Solution D

| Item Description | Lot Number/Batch | Total Mass g | % Used |
|---|---|---|---|
| Lab D.I Water | | 175.0 | 87.5 |
| Dextralip 15 | Warnick & Co. | 0.80 | 0.4008 |
| Tris Buffer | | .0.62 | 0.31 |
| Sorbitol | Sigma-Item S-7547 Lot 70K0936 | 10.7 | 5.34 |
| Ph Adjustment | 5N NaOH/3.25N HCl | Adjust pH to target 7.20 | |
| Total QS to Final Weight | | 200.00 | |
| Cloud Point | | | |

TABLE E

Asymmetric Membrane (BTS-SP-300)
Solution Selectivity: Solution E

| Item Description | Lot Number/Batch | Total Mass g | % Used |
|---|---|---|---|
| Lab D.I Water | | 175.0 | 87.5 |
| PVA 30-70K | | 2.0 | 1.0 |
| Mops Buffer | Sigma: Item M-1254; Lot 5450 | 1.0 | .5 |
| Sorbitol | Sigma-Item S-7547 Lot 70K0936 | 3.0 | 1.5 |
| Sucrose | Sigma-Item S-5016 | 3.0 | 1.5 |
| MgC12*6H20 | Sigma: Item M-9272; Lot 70K09321 | 1.0 | .5 |

TABLE E-continued

Asymmetric Membrane (BTS-SP-300)
Solution Selectivity: Solution E

| Item Description | Lot Number/Batch | Total Mass g | % Used |
|---|---|---|---|
| pH Adjustment | 5.0N NaOH/HCl | Adjust pH to target 6.40 | |
| Total | | 30.00 | |
| Cloud Point | 1% MOPS - 48 mM | | |

A sheet of material 54 was made in the following manner based on the solution composition identified in Table D. A dextran sulphate sodium salt in the form of Dextralip™ 15, which has a molecular weight of about 12,000, TRIS buffer (TRIS Hydroxymethyl Aminomethane) and sorbitol were added to deionized (DI) water in the amounts shown in Table D, then mixed and adjusted for pH as indicated in the table to make the impregnation solution. As known in the art, pH was adjusted as necessary to the acidic side with 3.25 N HCl. The final impregnation solution was QS'ed (adjusted with Quantity Sufficient) with D.I. water, to the final target weight as set forth in Table D. The pH was again tested and adjusted as required by the methods previously disclosed. The Accuwick Ultra™ material was dipped into this solution and was hung vertically to allow the excess solution to drip off the material. Alternatively, larger membrane treatments are accomplished by the use of a drying tunnel in either the vertical, horizontal, or inclined arrangement. In practice, the material was then dried in an inclined position in a drying tunnel at between 70° F. and 100° F., and more preferably between 80° and 90° F., for 9 minutes to 18 minutes.

A sheet of material 56 was made in the following manner. Mops buffer, sorbitol, sucrose, $MgCl_2.6H_2O$ and polyvinyl alcohol 30-70K were added to DI water in the amounts shown in Table E. A sheet of BTS, an asymmetric polysulfone membrane, was dipped into this solution and was hung vertically to allow the excess solution to drip off the material and allowed to dry at room temperature. Alternatively, larger membrane treatments are accomplished by the use of a drying tunnel in either the vertical, horizontal, or inclined arrangement. Preferably, the material is dried in an inclined position in a drying tunnel at between 70° F. and 90° F., and more preferably between 750 and 85° F., for 9 minutes to 18 minutes.

Figure 7:
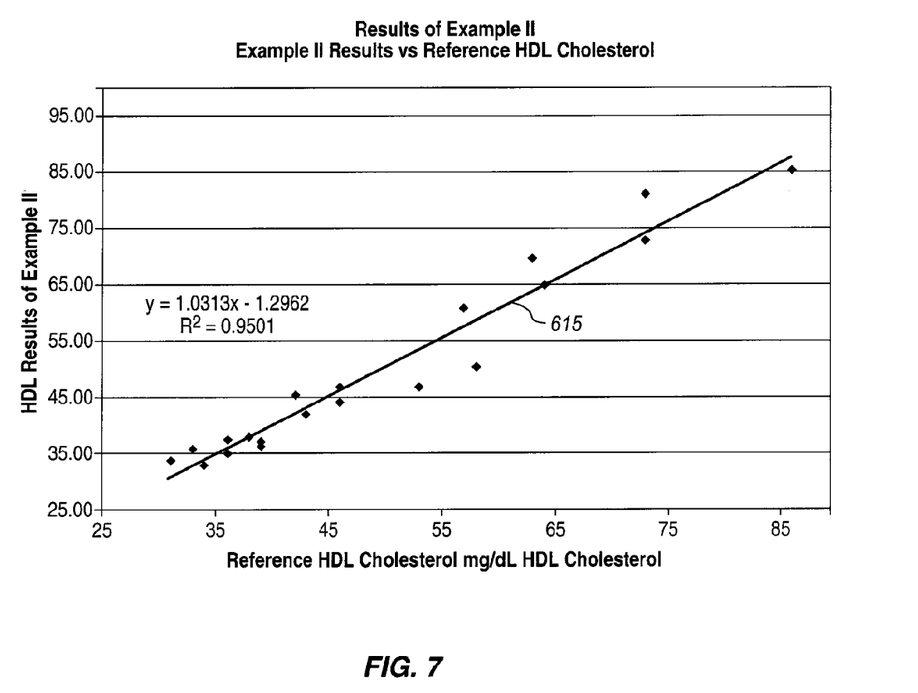
FIG. 7 is a graph of HDL cholesterol readings from a dry test strip according to the invention plotted along the ordinate versus reference HDL cholesterol for the same sample plotted along the abscissa.

A test strip assembly 50 was made by assembling a sheet of SEFAR™ type 76 SK 022, the above two sheets, and a sheet of Biodyne™ A material made as discussed in Example I. Circular blanks were cut out and were inserted in a test assembly 20 as shown in FIGS. 3-9. In a manner known in the art, a curve similar to that shown in FIG. 6 was then constructed using reflectance measurements from a standard laboratory test for HDL. As also known in the art, the curve was then used to program a Bioscanner 2000 reader available from Polymer Technology Systems, Inc., Indianapolis, Ind. The reader was then successfully used to directly read HDL concentrations in milligrams per deciliter (mg/dl) from a test assembly as described above. FIG. 7 illustrates the results using strips constructed as described in Example II above. FIG. 7 is a graph of the HDL cholesterol readings directly read from the reader plotted along the ordinate versus reference HDL cholesterol for the same sample plotted along the abscissa. The line 615 shows where the results would lie if the strip according to the invention gave identical results to the reference test. As can be seen, the plotted points lie very close to the line, and the scatter is essentially random. This is an excellent result since even if the results from two identical reference tests were plotted there would be some scatter. These results show that the dry strip test according to the invention is highly accurate.

Figure 8:
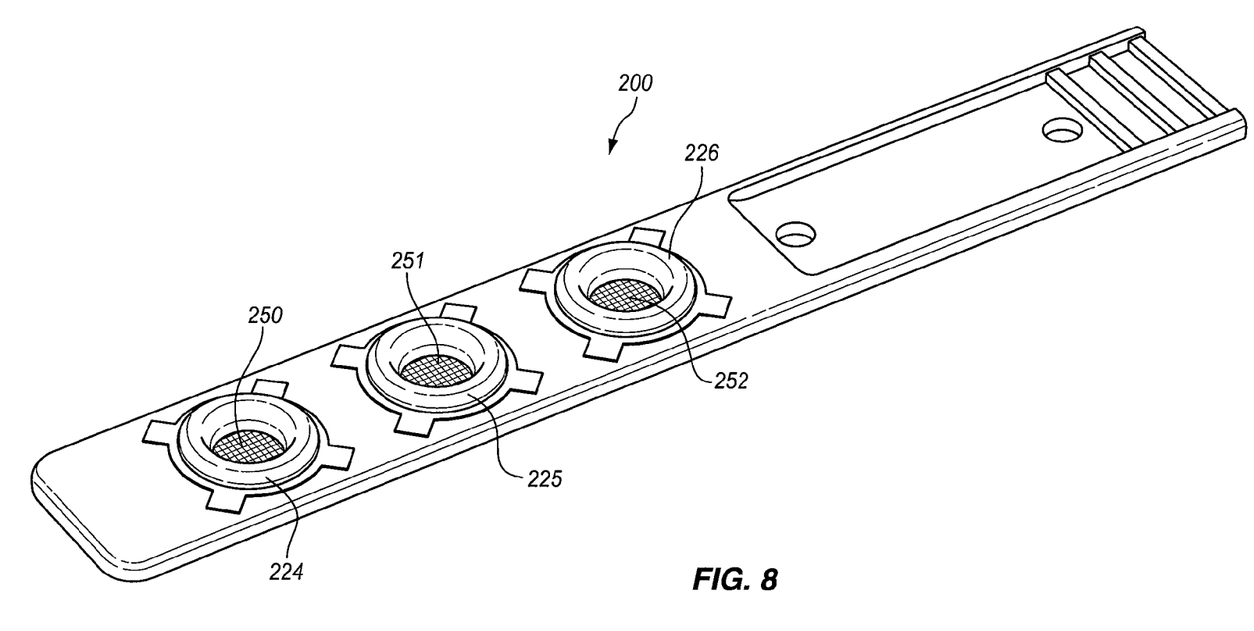
FIG. 8 illustrates another preferred embodiment of a test assembly according to the invention in which there are a plurality of strip holders and test strips.

FIG. 8 illustrates another preferred embodiment of a test assembly 200 according to the invention. This embodiment is provided to illustrate that once the design strategy of a non-precipitating dry strip test is disclosed as it has been above, many other non-precipitating dry strip tests can be designed by those skilled in the art. Test assembly 200 is similar to test assembly 20 except there are a plurality of strip holders 224, 225, and 226 each holding a different test strip 250, 251, and 252. Each of the strip holders 224, 225, and 226 have the same structure as strip holder 24. The test strips 250, 251, and 252 preferably have a plurality of layers, and more preferably four layers like test strip 50, though each generally will be impregnated with different chemistry. In particular, the chemicals in the depth filter layer (layer 54 in FIG. 1) will generally be different. In one alternative preferred embodiment, there are two strip holders 224 and 225 each having a different test strip 250 and 251. In this embodiment, test strip 250 contains chemicals for an assay to determine the concentration of HDL+LDL cholesterol, while test strip 251 contains chemicals to determine HDL cholesterol concentration, and the results for test strip 251 are subtracted from the results for test strip 250 to give HDL+LDL−HDL or LDL concentration. From the design strategy disclosure above, one skilled in the art will see that, in this embodiment, an HDL+LDL test strip can be made using an anionic polymer that is larger and has a smaller surface charge density than used for the HDL test described above, and/or surfactants specific to both HDL and LDL. The HDL test strip 251 is the same as the HDL test strip disclosed above.

In another embodiment, test strips 250 and 251 can be used to determine HDL+LDL−HDL=LDL as in the above paragraph, while test strip 252 is used to determine an independent LDL concentration as discussed above. The two LDL concentrations can then be averaged to give a very accurate LDL result because it is determined by two different methods. In this case, the HDL+LDL test strip 250 is as described in the paragraph above, while the HDL test strip 251 and LDL test strip 252 are as disclosed in the LDL chemistry section above.

A feature of the invention is that each layer of the test strip assembly, such as 50 and 450, is engineered to perform specific functions, and at the same time the various layers cooperate so that the test strip assembly as a whole operates to provide more accurate and reliable results. The layers together operate to create a vertical flow of sample liquid essentially across the entire test strip assembly. The red blood cells tend to move slower than the rest of the sample, or get removed from the sample in the layers 54, 56, 454, 456, and therefore, during the time in which the calorimetric reagent is reacting, will be contained in the layers above the reaction layer and will not be in the reaction layer 58, 458. However, the other analytes may or may not be in the reaction layer 58, 458. Since they are rendered non-reactive by the reagents in layer 54, 454, whether or not they are present is not of great importance. Since the non-desired analytes are not precipitated, the pores or channels in the layers 56, 58, 456, 458, and 460 remain open. This allows the sample liquid in the layers 56, 456, 460 adjacent to the reaction layer 58, 458 to participate in the calorimetric reaction. That is, in the embodiment of FIGS. 1 and 4, the majority of the liquid in a layer, such as 56, just above the layer 58, and, in the embodiment of FIG. 5, the majority of the liquid in the layer 456 just above the layer 458 and the majority of the liquid in the layer 460 just below the layer 458, is free to flow into the reaction layer 58, 458 and take part in the calorimetric reaction. This feature creates a larger volume of treated plasma or other bodily liquid. The larger volume directly results in a more accurate measurement. This feature allows the reaction layer 58, 458 to be much thinner than prior art reaction layers and still yield an accuracy associated with reaction layers that are much thicker.

Another feature of the invention is that the structures of the invention create a sample container, 80, 189, 280, 380, and 480, the sidewalls and bottom of which essentially do not pass liquid, and the top of which is open. This creates several advantages that result in a more accurate and reliable measurement. First, it results in a well-defined test volume of sample fluid. When the bodily fluid is added to the container, it flows to the bottom, and then stops. Only the bodily fluid in the reagent layer, and the adjacent layers in test strips in which the open pore feature discussed above is used, takes part in the reaction. Moreover, at the time of the reaction, this volume is essentially quiescent. Thus, a defined volume of fluid participates in the reaction. This duplicates much more closely the laboratory type test in which a beaker with a defined volume is used in tests, as compared to prior art test strips in which flow, particularly transverse flow, continued to occur during the test, which flow could depend on many variables and was difficult to quantify. Moreover, the fact that flow stops prevents red blood cells from getting through the layers above the test layers. That is, once flow stops, there is no flow or pressure to move the red blood cells. Thus, the layers above the test layer do not have to be completely impenetrable to red blood cells. All they have to do is slow the red blood cells for a while until the test volume is filled. This again plays back into the feature that the red blood cells do not completely block the pores, but permit ease of fluid flow once the reagent is reconstituted. In general, the object of the layers 54 and 56 is to contain the red blood cells in this region, and not permit them to get into the reaction layer 58. However, the containment of the red blood cells in layers 54 and 56 does not have to be absolute. Preferably, the containment of the red blood cells is at least 50%, more preferably it is at least 80%, and most preferably it is at least 95%.

In the inventive test, if more bodily fluid than is required for the test is placed in the sample port, such as 45, the fluid in excess of what is required for the test simply fills up the upper portion of the container, such as 80, and does not affect the test. If the excess is too much even for the container, the excess simply overflows the brim 46 and does not affect the test. Thus, the bodily fluid analysis system according to the invention is much less sensitive to the amount of bodily fluid supplied than prior art systems.

The above feature of the invention, i.e., that the test strip holder 24 provides a sample container 80, the sidewalls and bottom of which essentially do not pass liquid and therefore the test is performed on a well-defined volume of fluid, also increases the accuracy of the test because it provides a definitive end point to the test. As disclosed in U.S. Pat. No. 5,597, 532, which is incorporated herein by reference as though fully disclosed herein, a pseudo end can be determined from measurements of the reflectance through sensor port 36. The pseudo end point is defined as the point on the curve where the change in percent reflectance per unit time becomes smaller than a predetermined amount; that is, the slope of the reflectance versus time curve becomes less than a predetermined slope. However, in the prior art after the pseudo end point, the reflectance continues to drop for a considerable time because the reaction continues. This is largely due to the fact that plasma continues to leach through the sides of the strip.

For this strip holder according to the invention, the percent reflectance versus time curve reaches a minimum and then begins to curve upward. This is because only a well-defined amount of plasma takes part in the reaction, and after that plasma reacts, the color begins to fade as the reactants that produce the color oxidize or otherwise begin to break down, and the slope of the reflectance versus time curve becomes zero. The minimum defines an effective end point that is much easier to measure than a pseudo end point. For example, one can set the electronics to select the effective end point when the value of percent reflectance increases for a predetermined number of measured points, for example three points each taken a second apart. Generally, one will require more than just one increased value of the percent reflectance to determine the effective end point because random noise and other factors can lead to a single increased value for the curve when the curve is actually still continuing downward. The easier to measure minimum contributes to the increased accuracy of the test strip according to the invention.

Another feature of the invention is that the bottommost layer, such as 58 and 460, which forms the bottom of container 80, preferably does not pass liquid, but passes gases, such as air. This feature prevents air from being trapped at the bottom of the container, such as 80, when the bodily fluid is added. Any air that does not bubble out of the container is forced downward and out of the bottom of the container by the flow of bodily fluid. This removes an unquantifiable variable from the test and makes the test more accurate and reliable.

A related feature of the invention is that the test strip holder provides a controlled region for vertical flow of the bodily fluid sample. These features, alone and in combination, eliminate or sharply limit leaching or lateral flow of the sample as bodily fluid flows vertically through the layers. This degree of control translates to the ability to obtain accurate test readings from a reduced blood sample. Accurate results can be obtained with a sample size of as low as 4 ml and as great as 40 ml with the present invention.

Another feature of the invention is that the chemical process is non-precipitating. Precipitation creates particles of precipitate that would tend to clog pores in the test strip 50. Clogging pores impedes the flow of the analyte to the detection membrane, and is not fully predictable, and thus leads to a non-uniform color development. Clogging by precipitates also competes with the filtration of the red blood cells and makes this desirable filtration less effective. A related feature is that the chemistry makes the non-selected bodily fluid components unreactive with the detection compound that creates the calorimetric response. That is, the non-selected bodily fluid components continue to flow in the test strip 50, but are taken out of the detection reaction.

A further feature of the invention is that the test strip assembly, such as 50, preferably does not include any glue, adhesive, or other substance to hold it in place. Such substances can get into the test sample and compromise the test to make it less accurate and reliable.

Another feature of the invention is that the reagents used, particularly those in layer 54, are non-hemolytic. That is, they will not rupture the red blood cells. This prevents the matter from inside the red blood cells from compromising the test. Preferably, the reagents are hypertonic; that is, the reagent in solution has a higher osmotic pressure than the osmotic pressure within the red blood cells. Thus, if there is any flow of water, it will be from within the cell to outside the cell. The reverse could cause the cells to gain water until they rupture. However, the reagents are selected so that the degree of hypertonicity is low. Otherwise, the liquid from with the blood cells could dilute the bodily fluid to be analyzed.

Another feature of the invention is that the interrelationship between reagent formulation and the liquid flow in the materials of the test strip layers is considered. That is, the effect of the reagent on the surface tension of the fluid, and the effect of the resulting surface tension on the rate of flow through the layers are considered. For example, water will generally not flow easily in the layers according to the invention. The membranes, in particular, tend to hold water like a sponge. However, water with the reagents dissolved flows easily in these membranes. This feature helps keep the liquid in the depth filter until the reagents are dissolved.

The test strips, such as 50 and 450, according to the invention are highly sophisticated compared to the prior art test assemblies. The prior art test strips tended to simply include materials, such as fiberglass, that could hold a large amount of bodily fluid and reagent. They succeeded largely because they used large amounts of both bodily fluid and reagent. In contrast, the test strip assemblies according to the invention utilize many different materials that are carefully chosen and engineered, and succeed because they better isolate the desired reaction. Because of this, the test strip assemblies of the invention can operate effectively with a much smaller amount of reagent, and thus are more economical than the prior art test strips.

The design methodology of the invention is a self-consistent and self-reinforcing process. The materials and chemical processes of the invention are carefully engineered so that more accurate and more reliable results can be achieved with a smaller amount of reagent and a correspondingly smaller test strip assembly. Because the results that can be achieved are more accurate and can be achieved with a smaller amount of reagent, more flexibility is permitted in the selection of materials in the layers and the reagents. For example, membranes that retain and hold relatively small amounts of liquid can be selected over fabrics that hold large amounts of fluid, while fabrics that hold large amounts of fluid can also be used advantageously where appropriate. The ability to use a wider variety of materials enables the engineer to design a test that is closely akin to a laboratory analysis. That is, laboratory analyses can be very accurate because the order and timing of the reactions can be carefully controlled. One can add an accurately measured amount of a first reactant to an accurately measured amount of solvent, allow a first reaction to occur, then add an accurately measured amount of second reactant and perform a second reaction, and so on. The ability to use a wide variety of different materials allows one to control the order and timing of the reactions in a similar manner. The first reaction is placed closest to the top in the vertical structure of the test strip assembly. The timing of the second reaction can be controlled by choosing the materials of the first reactant layer and the adjoining layers to control the flow time through the layers, and so on.

While the invention has been disclosed in terms of an HDL or LDL direct assay, it will be evident to those skilled in the art that many aspects of the invention will be useful in other assays. Now that a dry test strip assay has been disclosed that mimics many of the features of a laboratory assay, such as use of a well-defined test volume, reaction order and timing controls using a variety of materials, and the ability to remove red blood cells from the reaction while still providing the above two features, these features may also be used to test for total cholesterol, triglycerides, and many other analytes. Further, now that the advantages of a non-precipitating dry test strip, asymmetric membranes, removal of red blood cells from the detection area without filtering that can clog the system, these features can also be advantageously used for testing of other analytes. Further, although the description has disclosed specific exemplary material layers that perform the features of the invention, now that the functions of the layers and the interrelationships of the layers has been described, many other materials can be substituted which will perform the same functions. In addition, while the invention has been disclosed in terms of specific exemplary reactants, many other reactants that perform the same functions and have some or all of the same advantages can be substituted. Again, while the invention has been disclosed in terms of a particular bodily fluid, i.e., blood and blood plasma, many features of the invention will be useful in testing other bodily fluids, such as urine. Thus, the invention should not be limited to these specific structures, layer materials, reactants, and bodily fluids.

While the invention has been illustrated and described in detail in the drawings and foregoing description, the same should be considered as illustrative and not restrictive in character. It is understood that only the preferred embodiments have been presented and that all changes, modifications, and further applications that come within the spirit of the invention are desired to be protected.

For instance, while the illustrative embodiments only show a single sample application port and a single corresponding sensor port, multiple sample ports and multiple sensor ports are contemplated.

There has been described a novel in vitro, dry test system that is useful to assay for HDL, LDL, and other analytes. It should be understood that the particular embodiments shown in the drawings and described within this specification are for purposes of example and should not be construed to limit the invention, which will be described in the claims below. Further, it is evident that those skilled in the art may now make numerous uses and modifications of the specific embodiments described, without departing from the inventive concepts. For example, other non-precipitating chemistries may be used. Equivalent chemicals, membranes, or materials may be substituted. The chemicals may be distributed among a lesser or greater number of layers. The layers may be combined, or a plurality of layers may perform the function of one described herein. The non-precipitating chemistry and/or any of its novel features may be used to determine characteristics of other analytes. The non-precipitating chemistry may be used with dry test strips in which electrical parameters, such as resistance, may be altered by the test to indicate the characteristic. It is also evident that the methods recited may in many instances be performed in a different order; or equivalent structures and processes may be substituted for the various structures and processes described. Consequently, the invention is to be construed as embracing each and every novel feature and novel combination of features present in and/or possessed by the bodily fluid analysis system herein described.

What is claimed as new and desired to be protected by Letters Patent of the United States is:

1. A dry test strip for determining a characteristic of a selected analyte in blood, said dry test strip comprising:
   a reaction layer including chemicals that will react with said blood to determine a characteristic of a selected analyte in said blood, the reaction layer oriented under the blood separation layer, wherein the red blood cells are slowed or stopped from reaching said reaction layer; and
   said dry test strip further containing complexing chemicals that complex one or more non-selected analytes to prevent them from participating in said reaction without precipitating them, wherein said selected analyte is low density lipoprotein, said complexing chemicals including dextran sulphate, a divalent metal, and a destabilizing compound and wherein the complexing chemicals are added prior to the reaction layer.

2. A dry test strip as in claim 1 wherein said destabilizing compound is selected from the group consisting of glycols, polypropylenes, and polyethylenes.

3. A dry test strip as in claim 1 wherein said destabilizing compound is a polyoxyethylene-polyoxypropylene-polyoxyethylene hybrid.

4. A dry test strip as in claim 3 wherein said destabilizing compound has a molecular weight between 2,100 and 6,000.

5. A dry test strip as in claim 3 wherein said destabilizing compound has a preponderance of polyoxyethylene.

6. A dry test strip as in claim 1 wherein said complexing chemicals include a gentle surfactant.

7. A dry test strip as in claim 1 wherein said complexing chemicals include 3-{[3-Cholamidopropyl]dimethylammonio}3-propane-sulfonate.

8. A dry test strip as in claim 1 wherein the complexing chemicals are introduced above the reaction layer, such that as the complexed and non-selected analytes flow through the test strip, they are slowed or retained.

9. A dry test strip as in claim 1 wherein said dextran sulfate has a molecular weight between 50,000 and 8,000.

10. A dry test strip as in claim 1 wherein said dextran sulfate has a molecular weight between 25,000 and 10,000.

11. A dry test strip as in claim 1 wherein said dextran sulfate has a molecular weight between 18,000 and 12,000.

* * * * *